United States Patent [19]

Entwistle

[11] 4,131,449
[45] Dec. 26, 1978

[54] PROPANIMIDOTHIOIC ACID DERIVATIVES

[75] Inventor: Ian D. Entwistle, Sittingbourne, England

[73] Assignee: Shell Oil Company, Houston, Tex.

[21] Appl. No.: 842,772

[22] Filed: Oct. 17, 1977

[51] Int. Cl.² .................. A01N 9/36; A01N 9/12; A01N 9/14; C07C 119/00
[52] U.S. Cl. .................. 71/98; 260/453 RW; 71/87; 71/103; 260/551.5
[58] Field of Search ............ 260/453 RW; 71/98, 87, 71/103

[56] References Cited
FOREIGN PATENT DOCUMENTS 1254381 11/1971 United Kingdom.

Primary Examiner—Joseph Paul Brust

[57] ABSTRACT

Compounds of the formula

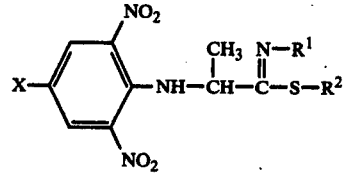

wherein X is hydrogen, halogen or alkyl optionally substituted by halogen and $R^1$ and $R^2$ each is alkyl, or acid addition salts thereof, are useful as herbicides.

9 Claims, No Drawings

PROPANIMIDOTHIOIC ACID DERIVATIVES

The invention relates to new propanimidothioic acid derivatives, their use as herbicides and to herbicidal formulations containing these acid derivatives.

SUMMARY OF THE INVENTION

The present invention is directed to new compounds, useful as herbicides, having the formula I

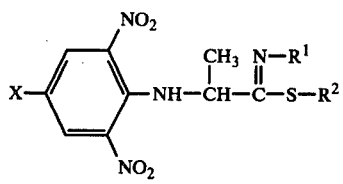

wherein X is a hydrogen atom, a halogen atom or an alkyl group optionally substituted by one or more halogen atoms and $R^1$ and $R^2$ each independently is an alkyl group, or an acid addition salt thereof.

Typical species contemplated within the scope of the invention include:
- S-methyl N-propyl-2-(4-fluoro-2,6-dinitroanilino)-propanimidothioate hydrobromide addition salt,
- S-ethyl N-methyl-2-(4-butyl-2,6-dinitroanilino)-propanimidothioate,
- S-ethyl N-ethyl-2-(4-chloro-2,6-dinitroanilino)-propanimidothioate methyl hydrosulfate addition salt, and
- S-propyl N-methyl-2-(4-trifluoromethyl-2,6-dinitroanilino)propanimidothioate hydroiodide addition salt.

It will be appreciated that the compounds of formula I have an asymmetric carbon atom and therefore can exhibit optical isomerism. The individual isomers and/or mixtures thereof are included within the scope of the invention. It will also be appreciated that certain isomers of the compounds of formula I may have more herbicidal activity than other isomers or mixtures thereof and that it can be desirable to effect separation of the more active isomer.

The compounds of the invention are conveniently prepared from 2-(2,6-dinitroanilino)thiopropanamides. For example, the appropriate thiopropanamide can be reacted with a reagent such as an alkyl halosulfonate, dialkyl sulfate, trialkyl oxonium tetrafluoroborate, or the like. If the acid addition salt is prepared first, it can be converted to the free base by treatment with, e.g., aqueous sodium bicarbonate.

The 2-(2,6-dinitoranilino)thiopropanamides can be prepared by procedures known in the art beginning with the appropriate 2-(2,6-dinitroanilino)propionamide. This starting material is reacted with phosphorus pentasulfide, preferably in the presence of a solvent such as tetrahydrofuran at room temperatures.

Preferred because of their herbicidal properties are the compounds of formula I wherein X is a hydrogen atom, a halogen atom having an atomic number of from 9 to 35, inclusive, or an alkyl group containing from 1 to 6 carbon atoms optionally substituted by from 1 to 3 halogen atoms having an atomic number of from 9 to 35, inclusive, for example, chlorine, bromine, methyl, ethyl, trifluoromethyl and the like; and $R^1$ and $R^2$ each independently is an alkyl group containing from 1 to 3 carbon atoms, or an acid addition salt thereof.

Generally more active and therefore most preferred are those compounds of formula I wherein X is a hydrogen atom or methyl and $R^1$ and $R^2$ each independently is methyl or ethyl, or an acid addition salt thereof.

The acid addition salts are prepared from inorganic or organic acids. Suitable inorganic acids include hydrohalogenic acids such as hydrochloric and hydrobromic, sulfoxy acids such as sulfuric, fluorosulfonic, phosphorus acids such as phosphoric, and nitrogen acids such as nitric, or boron acids such as boric or borofluoric acid. Suitable organic acids lower alkanoic, alkanesulfonic, alkenoic, alkendoic, hydroxyalkanoic, alkanedioic acids, or benzene acids, for example, maleic, fumaric, citric, tartaric, methanesulfonic, ethanesulfonic, acetic, or crotonic acids.

The thiopropanamides of the formula

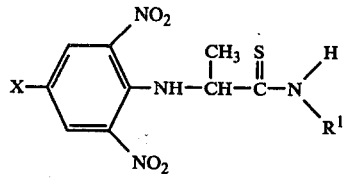

wherein $R^1$ is ethyl or higher and X is hydrogen, halogen or alkyl optionally substituted by halogen as previously defined are novel compounds and also possess useful herbicidal properties.

The compounds of the invention including the acid salts thereof have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broadleaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers and natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensaxion products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surfaceactive agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal, properties.

The method of applying the compounds of this invention comprises applying a compound of Formula I, ordinarily in a composition of one of the aforementioned types, to a locus or area to be protected from undesirable plant growth such as the foliage of the plants or the plant growth medium, e.g., soil in which the plant is growing or is to be grown. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of the compounds, intermediates and final, were confirmed by elemental analysis, and infrared and nuclear magnetic spectral analyses. The examples are for the purpose of illustration only and should not be regarded as limiting the invention in any way.

EXAMPLE 1 —
2-(2,6-Dinitro-4-methylanilino)-N-ethylthiopropionamide

To a solution of 11.5 g of 2-(2,6-dinitro-4-methylanilino)-N-ethylpropionamide in 150 ml of tetrahydrofuran was added in one portion at room temperature 9.5 g of phosphorus pentasulfide. The reaction mixture was stirred at room temperature and after ½ hour the excess phosphorus pentasulfide was filtered off and the filtrate was concentrated leaving an oil. This oil was taken up in ethanol and triturated with water. The resulting solid was isolated and azeotroped with toluene to leave 10.2 g of an orange solid. The solid was crystallized from toluene to give 7.1 g of the desired product as an orange solid, m.p. 121–123° C.

EXAMPLE 2 — S-methyl
d-2-(2,6-dinitro-4-methylanilino)-N-methyl-propanimidothioate hydrofluorosulfonate To a solution of 3.0 g of d-2-(2,6-dinitro-4-methylanilino)-N-methylthiopropionamide in 50 ml of methylene chloride was added in one portion 1.3 g of methyl fluorosulfonate. The reaction mixture was stirred continuously overnight at room temperature. The next day the reaction flask was scratched to produce a solid which was collected and air-dried to yield 4.0 g of product as a yellow solid; m.p. 138–140° C.

EXAMPLE 3 S-methyl d,1-2-(2,6-dinitro-4-methylanilino)-N-methyl-propanimidothioate A suspension 2.4 g of methyl d,1-2-(2,6-dinitro-4-methylanilino)-N-methylpropanimidothioate hydrofluorosulfonate in 50 ml of saturated NaHCO$_3$ solution and 10 ml of diethyl ether was allowed to stir at room temperature for 2 hours. The resulting phases were separated and the diethyl ether phase was dried and concentrated to leave 1.5 g of product as a yellow solid; m.p. 109–111° C.

Following procedures similar to those used in Examples 2 and 3, additional propanimidothioic acid derivatives were prepared as set forth in Table I.

Table I $$\underset{NO_2}{\underset{|}{X}}-\underset{}{\bigcirc}-NH-\underset{CH_3}{\underset{|}{CH}}-\underset{N-R^1}{\underset{\|}{C}}-S-R^2$$
(with second NO$_2$ on ring)

| Example | X | R$^1$ | salt | R$^2$ | % yield | M.P.; °C |
|---|---|---|---|---|---|---|
| 4 | CH$_3$ | CH$_3$ | — | CH$_3$ | 33 | 98–100 |
| 5 | CH$_3$ | C$_2$H$_5$ | HBF$_4$ | CH$_3$ | 51 | 80.5–82.5 |
| 6 | CH$_3$ | C$_2$H$_5$ | HBF$_4$ | CH$_3$ | 48 | 71–82 |
| 7 | CF$_3$ | CH$_3$ | — | CH$_3$ | 45 | 82–84 |
| 8 | CF$_3$ | CH$_3$ | HSO$_3$F | CH$_3$ | 82 | 143.5–144 |
| 9 | CH$_3$ | C$_2$H$_5$ | — | C$_2$H$_5$ | 51 | 56–58.5 |
| 10 | CH$_3$ | CH$_3$ | — | CH$_3$ | 98 | 94–96.5 |
| 11 | H | CH$_3$ | — | CH$_3$ | 100 | 68–70 |
| 12 | H | CH$_3$ | HSO$_3$F | CH$_3$ | 65 | 132.5–133 |
| 13 | CH$_3$ | CH$_3$ | HB(F)$_4$ | C$_2$H$_5$ | 75 | 157–158 |
| 14 | CH$_3$ | CH$_3$ | — | C$_2$H$_5$ | 60 | 94 |
| 15 | CH$_3$ | CH$_3$ | HSO$_3$F | CH$_3$ | 65 | 125 (with decomposition) |
| 16 | CH$_3$ | CH$_3$ | HSO$_3$F | CH$_3$ | 59 | 107–109 |

Example of Herbicidal Activity

The pre-emergence herbicidal activity of the compounds of the invention was evaluated by planting seeds of water grass, garden cress, downey brome, velvet leaf, yellow foxtail and sicklepod in test tubes, nominally measuring 25 × 200 millimeters, containing soil treated with the test compound at the rates of 0.1 and 1 mg per tube designated in Table II at Rates I and II respectively. The planted soil was held under controlled conditions of temperature, moisture, and light for 11 to 12 days. The amount of germination and growth in each tube were evaluated on a 0 to 9 scale, 0 rating indicating no effect, 9 death of the seedlings or no germination.

The post-emergence activity of the compounds of this invention was evaluated by spraying 7-day old crabgrass plants, 10-day old pigweed plants, 6-day old downey brome plants, 9-day old velvet leaf, 10-day old yellow foxtail plants, and 7-day old sicklepod plants to runoff with a liquid formulation of the test compound at the rates of 0.8 milliliter of an 0.025% solution designated Rate I in Table II, and 0.8 milliliter of an 0.25% solution designated Rate II in Table II. The sprayed plants were held under controlled conditions for 10 to 11 days and the effect of the test compound was then evaluated visually, the results being rated on the 0 to 9 scale described above.

The results of the pre- and post-emergence tests are summarized in Table II.

TABLE II
HERBICIDE SCREEN RESULTS

| | Pre-emergence (Soil) | | | | | | Post-emergence (Foliar) | | | | | |
|---|---|---|---|---|---|---|---|---|---|---|---|---|
| Example | Water-grass $I_{II}$ | Garden Cress $I_{II}$ | Downey Brome $I_{II}$ | Velvet Leaf $I_{II}$ | Yellow Foxtail $I_{II}$ | Sicklepod $I_{II}$ | Crab-grass $I_{II}$ | Pigweed $I_{II}$ | Downey Brome $I_{II}$ | Velvet Leaf $I_{II}$ | Yellow Foxtail $I_{II}$ | Sicklepod $I_{II}$ |
| 1 | — | $6_8$ | $8_9$ | $7_9$ | $8_9$ | — | $0_2$ | $0_5$ | $3_6$ | $5_9$ | $2_2$ | — |
| 2 | — | $7_9$ | $8_9$ | $7_9$ | $8_9$ | — | $7_9$ | $0_9$ | $0_0$ | $4_4$ | $9_9$ | — |
| 3 | — | $0_6$ | $0_8$ | $0_9$ | $4_9$ | — | $4_9$ | $4_7$ | $3_8$ | $5_7$ | $8_9$ | — |
| 4 | — | $8_9$ | $7_9$ | $7_9$ | $9_9$ | — | $0_4$ | $0_9$ | $0_7$ | $0_7$ | $7_7$ | — |
| 5 | — | $4_7$ | $7_9$ | $7_9$ | $8_9$ | — | $2_6$ | $4_8$ | $0_4$ | $0_7$ | $0_3$ | — |
| 6 | — | $0_8$ | $2_8$ | $6_6$ | $7_8$ | — | $0_2$ | $0_3$ | $0_0$ | $0_2$ | $2_8$ | — |
| 7 | — | $0_6$ | $0_3$ | $0_2$ | $0_8$ | — | $0_7$ | $0_5$ | $0_0$ | $0_0$ | $0_9$ | — |
| 8 | — | $0_9$ | $7_9$ | $6_9$ | $8_9$ | — | $5_9$ | $4_9$ | $0_1$ | $1_5$ | $4_4$ | — |
| 9 | — | $7_9$ | $8_9$ | $9_9$ | $9_9$ | — | $7_9$ | $8_9$ | $5_9$ | $6_8$ | $8_9$ | — |
| 10 | $0_9$ | $2_8$ | $5_9$ | $5_9$ | $4_9$ | $6_9$ | $8_9$ | $6_9$ | $6_8$ | $0_9$ | $9_9$ | $0_9$ |
| 11 | $1_7$ | $1_6$ | $4_9$ | $0_9$ | $5_9$ | $6_9$ | $2_9$ | $3_9$ | $0_8$ | $0_9$ | $9_9$ | $0_9$ |

I claim:
1. A compound of the formula

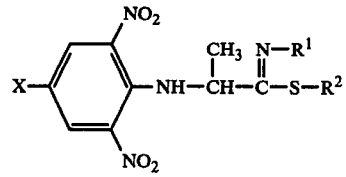

wherein X is a hydrogen atom, a halogen atom having an atomic number of from 9 to 35, inclusive, or an alkyl group containing from 1 to 6 carbon atoms optionally substituted by from 1 to 3 halogen atoms having an atomic number of from 9 to 35, inclusive, and R$^1$ and R$^2$ each independently is an alkyl group containing from 1 to 3 carbon atoms, or an acid addition salt thereof selected from hydrochloric, hydrobromic, sulfuric, fluorosulfonic, phosphoric, nitric, boric, borofluoric, maleic, fumaric, citric, tartaric, methanesulfonic, ethansulfonic, acetic or crotonic acid.

2. A compound according to claim 1 wherein X is a hydrogen atom or methyl and R$^1$ and R$^2$ each independently is methyl or ethyl, or an acid addition salt thereof.

3. A compound according to claim 2 which is the fluoroborate addition salt when X and R$^2$ are each methyl and R$^1$ is ethyl.

4. A compound according to claim 2 which is the fluoroborate addition salt when X is methyl and R$^1$ and R$^2$ are each ethyl.

5. A compound according to claim 2 wherein X, R$^1$ and R$^2$ are each methyl.

6. A compound according to claim 5 which is the fluorosulfate addition salt.

7. A herbicidal composition comprising a herbicidally effective amount of a compound according to claim 2 and at least one surface-active agent or carrier therefor.

8. A method for controlling undesirable plant growth at a locus which comprises applying to the locus to be protected a herbicidally effective amount of a compound according to claim 1.

9. A method according to claim 8 wherein the herbicidally effective compound is selected from S-methyl N-ethyl-2-(4-methyl-2,6-dinitrophenylamino)-propanimidothioate, S-ethyl N-ethyl-2-(4-methyl-2,6-dinitrophenylamino)-propanimidothioate tetrafluoroboric acid addition salt, S-methyl d-N-methyl-2-(4-methyl-2,6-dinitrophenylamino)-propanimidothioate fluorosulfonic acid addition salt, or S-methyl d,1-N-methyl-2-(4-methyl-2,6-dinitrophenylamino)-propanimidothiate.

* * * * *